(12) United States Patent
Werthmann et al.

(10) Patent No.: US 8,394,791 B2
(45) Date of Patent: Mar. 12, 2013

(54) CRYSTALLINE, ENANTIOMERICALLY PURE SALT FORM OF A BETA-AGONIST, AND THE USE THEREOF AS A DRUG

(75) Inventors: Ulrike Werthmann, Biberach (DE); Marco Santagostino, Mittelbiberach (DE); Adil Duran, Rigefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 195 days.

(21) Appl. No.: 12/918,374

(22) PCT Filed: Feb. 17, 2009

(86) PCT No.: PCT/EP2009/001082
§ 371 (c)(1),
(2), (4) Date: Nov. 4, 2010

(87) PCT Pub. No.: WO2009/103479
PCT Pub. Date: Aug. 27, 2009

(65) Prior Publication Data
US 2011/0262369 A1 Oct. 27, 2011

(30) Foreign Application Priority Data
Feb. 22, 2008 (EP) .................................. 08151842

(51) Int. Cl.
*C07D 265/00* (2006.01)
(52) U.S. Cl. ....................................... 514/230.5; 544/90
(58) Field of Classification Search ............ 544/90; 514/230.5
See application file for complete search history.

(56) References Cited

U.S. PATENT DOCUMENTS

| | | | |
|---|---|---|---|
| 4,341,778 A | 7/1982 | Mentrup et al. | |
| 4,460,581 A | 7/1984 | Schromm et al. | |
| 4,570,630 A | 2/1986 | Elliott et al. | |
| 4,811,731 A | 3/1989 | Newell et al. | |
| 4,950,767 A | 8/1990 | Kraatz | |
| 5,035,237 A | 7/1991 | Newell et al. | |
| 7,160,882 B2 | 1/2007 | Bouyssou et al. | |
| 7,220,742 B2 | 5/2007 | Lustenberger et al. | |
| 7,244,728 B2 | 7/2007 | Bouyssou et al. | |
| 7,423,146 B2 | 9/2008 | Santagostino et al. | |
| 7,709,474 B2 | 5/2010 | Konetzki et al. | |
| 2001/0008632 A1 | 7/2001 | Freund et al. | |
| 2005/0255050 A1 | 11/2005 | Trunk et al. | |
| 2006/0189605 A1 | 8/2006 | Konetzki | |
| 2007/0027148 A1 | 2/2007 | Lustenberger et al. | |
| 2007/0066607 A1 | 3/2007 | Fairhurst et al. | |
| 2007/0112191 A1 | 5/2007 | Santagostino et al. | |
| 2008/0051392 A1 | 2/2008 | Konetzki et al. | |
| 2008/0053430 A1 | 3/2008 | Nowak et al. | |
| 2010/0233268 A1 | 9/2010 | Trunk et al. | |

FOREIGN PATENT DOCUMENTS

| | | |
|---|---|---|
| CA | 1165317 A1 | 4/1984 |
| CA | 2164222 A1 | 12/1994 |
| CA | 2232151 A1 | 4/1997 |
| CA | 2233981 A1 | 4/1997 |
| CA | 2237853 A1 | 6/1997 |
| CA | 2300908 A1 | 4/1999 |
| CA | 2450961 A1 | 1/2003 |
| CA | 2425539 A1 | 4/2003 |
| CA | 2425560 A1 | 4/2003 |
| CA | 2471578 A1 | 8/2003 |
| CA | 2472149 A1 | 8/2003 |
| CA | 2474874 A1 | 8/2003 |
| CA | 2552784 A1 | 8/2005 |
| CA | 2562859 A1 | 11/2005 |
| CA | 2598914 A1 | 8/2006 |
| DE | 3625685 A1 | 3/1987 |
| DE | 3609152 A1 | 9/1987 |
| EP | 0043940 A1 | 1/1982 |
| EP | 0237507 A1 | 9/1987 |
| WO | 9114468 A1 | 10/1991 |
| WO | 9407607 A1 | 4/1994 |
| WO | 9428958 A1 | 12/1994 |
| WO | 9532937 A1 | 12/1995 |
| WO | 9712683 A1 | 4/1997 |
| WO | 9712687 A1 | 4/1997 |
| WO | 9720590 A1 | 6/1997 |
| WO | 9916530 A1 | 4/1999 |
| WO | 0230928 A1 | 4/2002 |
| WO | 0232898 A2 | 4/2002 |
| WO | 03000265 A1 | 1/2003 |
| WO | 03064417 A1 | 8/2003 |
| WO | 03064418 A1 | 8/2003 |
| WO | 03064419 A1 | 8/2003 |
| WO | 2004087142 A1 | 10/2004 |
| WO | 2005070908 A1 | 8/2005 |
| WO | 2005111005 A1 | 11/2005 |
| WO | 2006089859 A1 | 8/2006 |

(Continued)

OTHER PUBLICATIONS

International Search Report corresponding to WO 2009/103479, Oct. 9, 2009.

(Continued)

*Primary Examiner* — Kahsay T Habte
(74) *Attorney, Agent, or Firm* — Michael P. Morris; Edward S. Lazer

(57) ABSTRACT

This invention concerns a crystalline, enantiopure hydrochloride salt of N-(5-{2-[3-(4,4-diethyl-2-oxo-4H-benzo[d][1,3]oxazin-1-yl)-1,1-dimethyl-propylamino-1-hydroxy-ethyl}-2-hydroxy-phenyl)-methanesulfonamide, preferably of N-(5-{(R)-2-[3-(4,4-diethyl-2-oxo-4H-benzo[d][1,3]oxazin-1-yl)-1,1-dimethyl-propylamino-1-hydroxy-ethyl}-2-hydroxy-phenyl)-methanesulfonamide and its action as a long acting beta-agonist, alone or in combination with one or multiple other active ingredients for the treatment of respiratory diseases.

7 Claims, 3 Drawing Sheets

FOREIGN PATENT DOCUMENTS

| | | |
|---|---|---|
| WO | 2007/054484 A1 | 5/2007 |
| WO | 2008/023001 A1 | 2/2008 |

OTHER PUBLICATIONS

Bedi, Rajinder Singh; Inhaled Corticosteroids in COPD; Indian J. Chest Dis. Allied Sci. (2005) vol. 47 pp. 243-244.
Bloom, Jonathan, D., et al; Disodium (R,R)-5[2-[[2-(3Chlorophenyl)-2-hydroxyethyl]-amino]propyl]-1,3-benzodloxole-2,2-dicarboxylate (CL 316,243). A Potent Beta-Adrenergic Agonist Virtually Specific for Beta2 Receptors. A Promising Antidiabetic and Antiobesity Agent; Journal of medicinal Chemistry (1992) vol. 35 No. 16 pp. 3081-3084.
Braga, Dario, et al; Making Crystals from Crystals: A Green Route to Crystal Engineering and Polymorphism; The Royal Society of Chemistry, Chemical Communications (2005) Issue 29 pp. 3635-3645.
Bruice, Paula Yurkanis; Glossary: Organic Chemistry (1995) p. G-7.
Chandrasekharan, J., et al; The Reduction of Oximes by Lithium Aluminum Hydride in Hexamethylphosphoramide Solvent; J. Org. Chem (1985) vol. 50 pp. 5448-5450.
Clayden, James, et al; Organic Chemistry; 1st ed., (2000) Oxford University Press; Chapter 16 pp. 381-405.
Corey, Elias. J., et al; Reduction of Carbonyl Compounds with Chiral Oxazaborolidine Catalysts: A New Paradigm for Enantioselective Catalysis and a Powerful New Synthetic Method; Angew. Chem. Int. Ed, 1998, vol. 37 pp. 1986-2012.
Durham, Martha, C.; Tiotropium (Spiriva): A Once-Daily Inhaled Anticholinergic Medication for Chronic Obstructive Pulmonary Disease; BUMC Proceeding (2004) vol. 17 pp. 366-373.
Gavezzotti, Angelo; Are Crystal Structures Predictable? Accounts of Chemical Research (1994) vol. 27 pp. 309-314.
Guy, Alain, et al; Selective a-Chloroination of Alkyl Aryl Ketones; Synthesis 1982, 12, pp. 1018-1020.
Hamada, Takayuki, et al; Practical Synthesis of Optically Active Styrene Oxides via Reductive Transformation of 2-chloroacetophenones with Chiral Rhodium Catalysts; Org. Lett (2002) vol. 4 No. 24 pp. 4373-4376.
Hett, Robert., et al; Conformational Toolbox of Oxazaborolidine Catalysts in the Enantioselective Reduction of a-Bromo-Ketone for the Synthesis of (R,R)-Formoterol;Tetrahedron Letters (1998) vol. 39 pp. 1705-1708.
Hirao, Akira, et al; Asymmetric Reduction of Aromatic Ketones with Chiral Alkoxy-amine-borane Complexes; J. Chem. Soc. Chem. Comm (1981) pp. 315-317.
Hong, Yaping, et al; cis-1-Amino-2-indanol in Asymmetric Synthesis, Part I. A Practical Catalyst System for the Enantioselective Borane Reduction of Aromatic Ketones; Tetrahedron Lett., 1994, vol. 35, No. 36 pp. 6631-6634; Great Britain.
International Search Report and Written Opinion for PCT/EP2006/068157 mailed on Apr. 16, 2007.
International Search Report for Corresponding PCT/EP2007/058651 mailed Oct. 29, 2007.
International Search Report for PCT/EP2006/060033 mailed May 4, 2006.
International Search Report for PCT/EP2007/058653 mailed Oct. 29, 2007.
International Search Report for PCT/EP2007/058654 mailed Dec. 6, 2007.
International Search Report for PCT/EP2007/058655 mailed Oct. 29, 2007.
International Search Report for PCT/EP2009/001082 mailed Oct. 23, 2009.
Itsuno, Shinichi, et al; Asymmetric Reduction of Aliphatic Ketones with the Reagent Prepared from (S)-(-)-2-Amino-3methyl-1-1,1-diphenylbutan-1-o1 and Borane; J. Org. Chem (1984) vol. 49 pp. 555-557.
Itsuno, Shinichi, et al; Asymmetric Synthesis Using Chirally Modified Borohydrides, Part 1. Enantioselective Reduction of Aromatic Ketones with the Reagent Prepared from Borane and (S)-Valinol; J. Chem. Soc. Perkin Trans. I (1983) pp. 1673-1676.
K. Yutaka; 2-Amino-4-phenylthiazole derivatives as anti-atherogenic agents; Eur. J. Med. Chem. Chim.Ther (1981) vol. 16 pp. 355-362.
Kajigaeshi, Shoji, et al; z-Chloroination of Aromatic Acetyl Derivatives with Benzyltrimethylammonium Dichloroiodate; Synthesis Jul. 1988, vol. 7, pp. 545-546.
Koser, Gerald, F., et al; One-Step Alpha-Tosyloxylation of Ketones with [Hydeoxy(tosyloxy)iodo]Benzene; Journal of Organic Chemistry (1982) vol. 47 No. 12 pp. 2487-2489.
Lodaya, Jayant, S., et al; Direct a-Mesyloxylation of Ketones and b-dicarbonyl Compounds with [Hydroxy (mesyloxy)iodo] benzene; J. Org. Chem (1988) vol. 53 p. 210.
Masui, Moriyasu, et al; A Practical Method for Asymmetric Borane Reduction of Prochiral Ketones Using Chiral Amino Alcohols and Trimethyl Borate; Synlett, Mar. 1997, pp. 273-274.
Merck Manual Home Edition Article Entitled, "Influenza," Accessed on Feb. 22, 2010 at www.merck.com/mmhe/print/sec17/ch198/ch198d.html.
Merck Manual Home Edition Entitled, "Lung Cancer," accessed on Jul. 28, 2010 at www.merck.com/mmhe/print/sec04/ch057/ch057a.html.
Quallich, George, J., et al; Diphenyloxazaborolidine A New Catalyst for Enantioselective Reduction of Ketones; Tetrahedron Lett (1993) vol. 34 No. 26 pp. 4145-4148; Great Britain.
Quallich, George, J., et al; In Situ Oxazaborolidines, Practical Enantioselective Hydride Reagents;Synlett, Dec. 1993, p. 929.
Rao A. V. Rama., et al; Enantioselective Catalytic reductions of Ketones with New Four Membered Oxazaborolidines: Application to (S)- Tetramisole; Tetrahedron: Asymmetry (1992) vol. 3 No. 7 pp. 859-862; Elsevier Science Publisher.
Seddon, Kenneth, R; Pseusopolymorph: A Polemic; Crystal Growth & Design (2004) vol. 4, Issue 6 p. 1087, Web Release date Oct. 19, 2004.
Vedejs, Edwin, et al; A Tyrosine-Derived Benzofuranone Related to a Diazonamide A; Org. Lett (2000) vol. 2 No. 8 pp. 1031-1032.
Vippagunta, Sudha, R., et al; Crystalline Solids; Advanced Drug Delivery Reviews (2001) vol. 48 pp. 3-26.
Yu, Lian, et al; Physical Characterization of Polymorphic Drugs: An Integrated Characterization Strategy; Pharmaceutical Science & Technology Today (1998) vol. 1, No. 3 pp. 118-127.

Figure 1: XRPD - Diagram of the crystalline compound 1
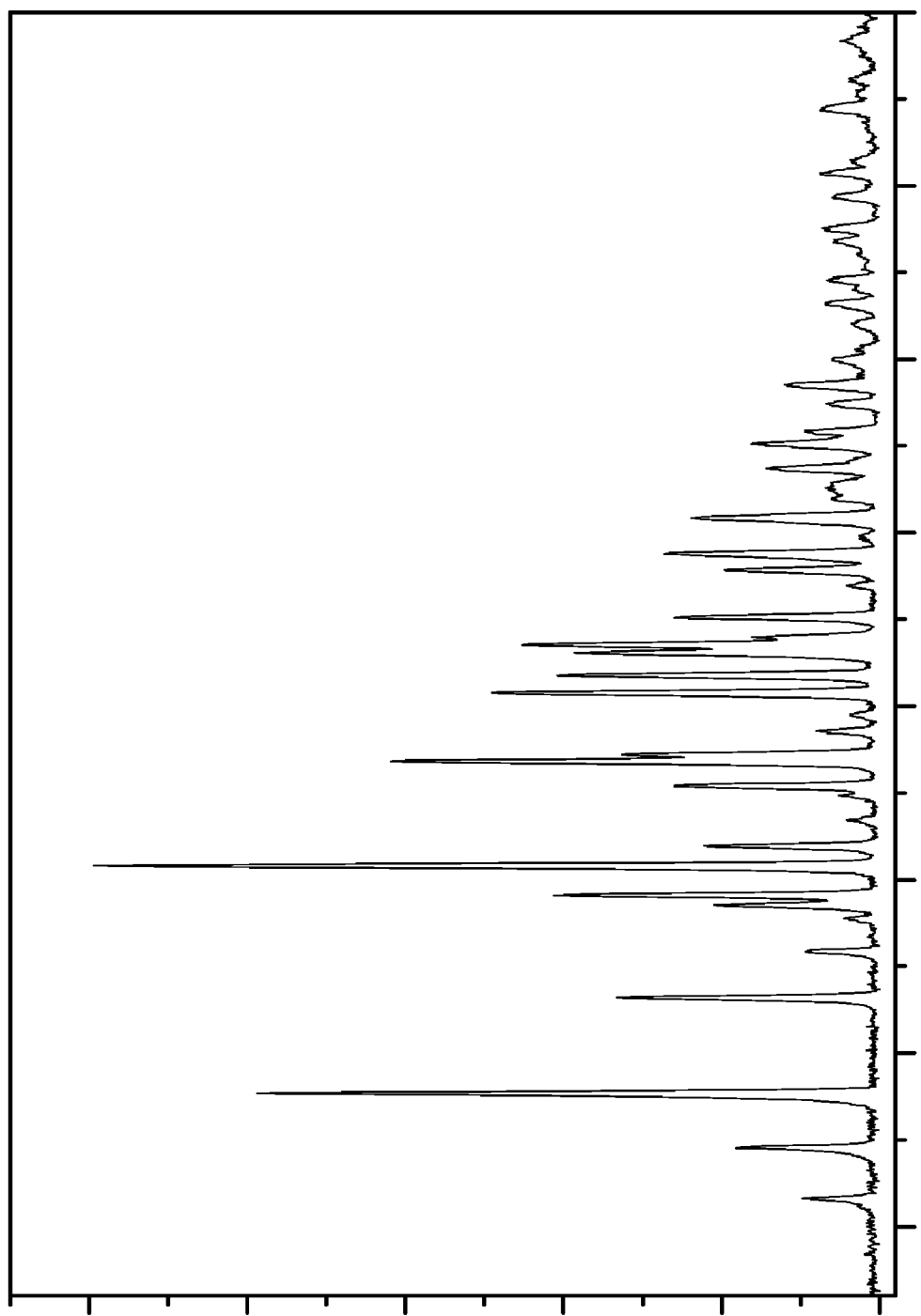

Figure 2: DSC/TG – Diagram of the crystalline compound 1
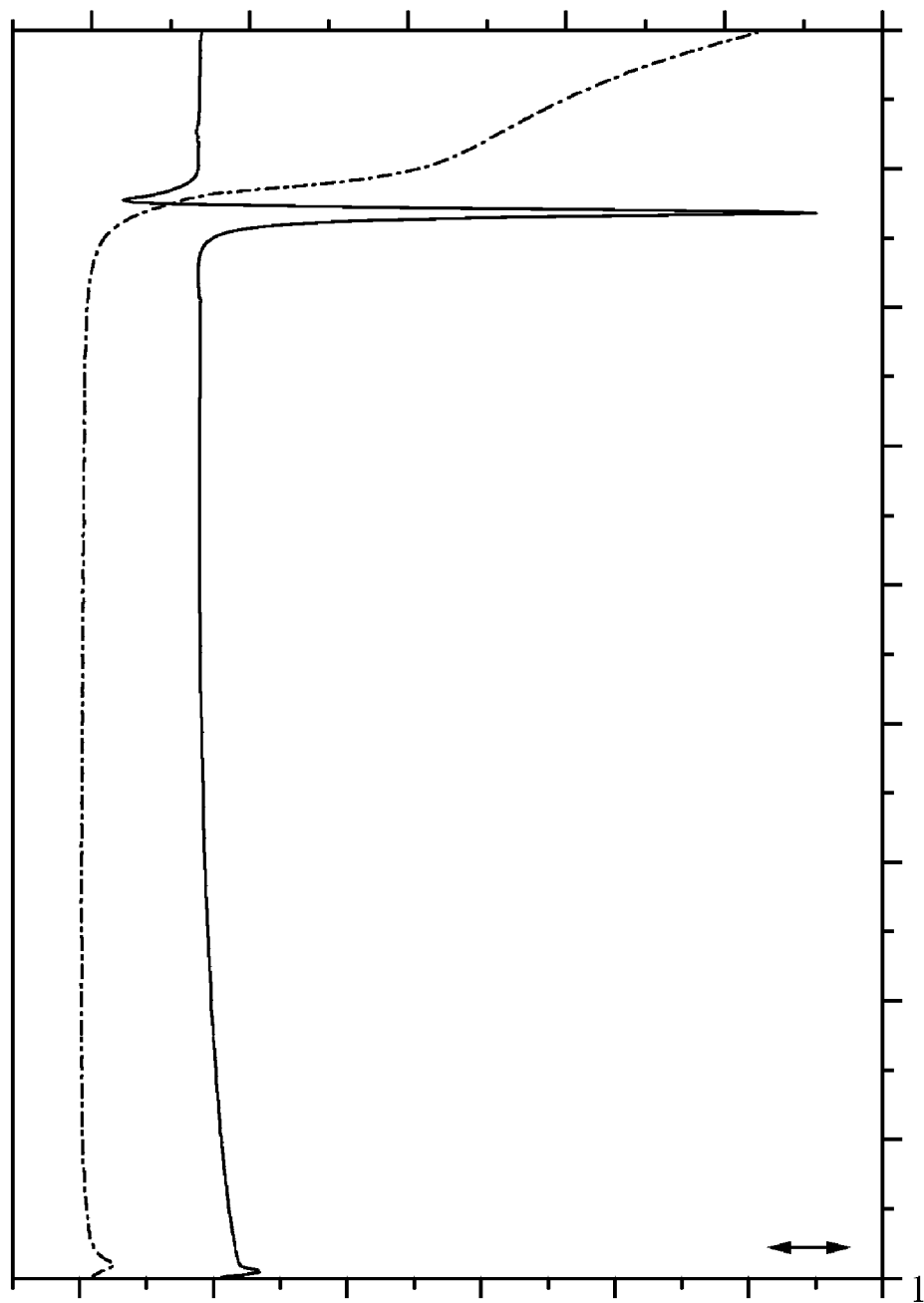

Figure 3: DVS-Diagrams of the crystalline compound 1
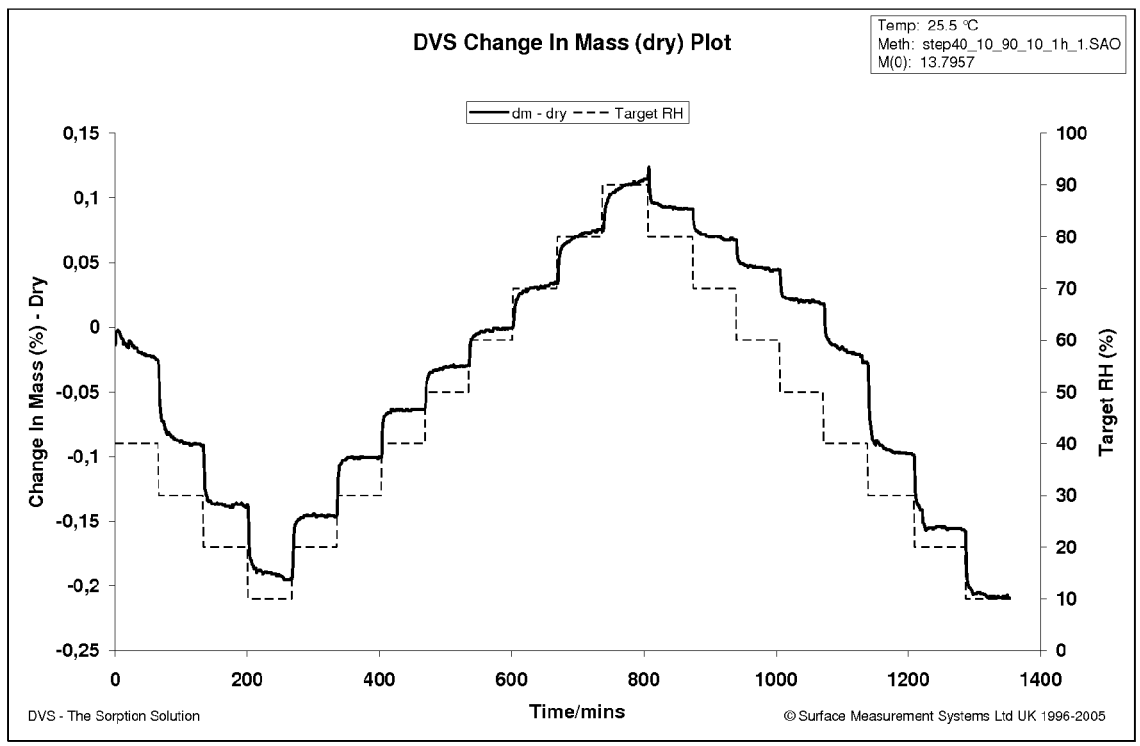
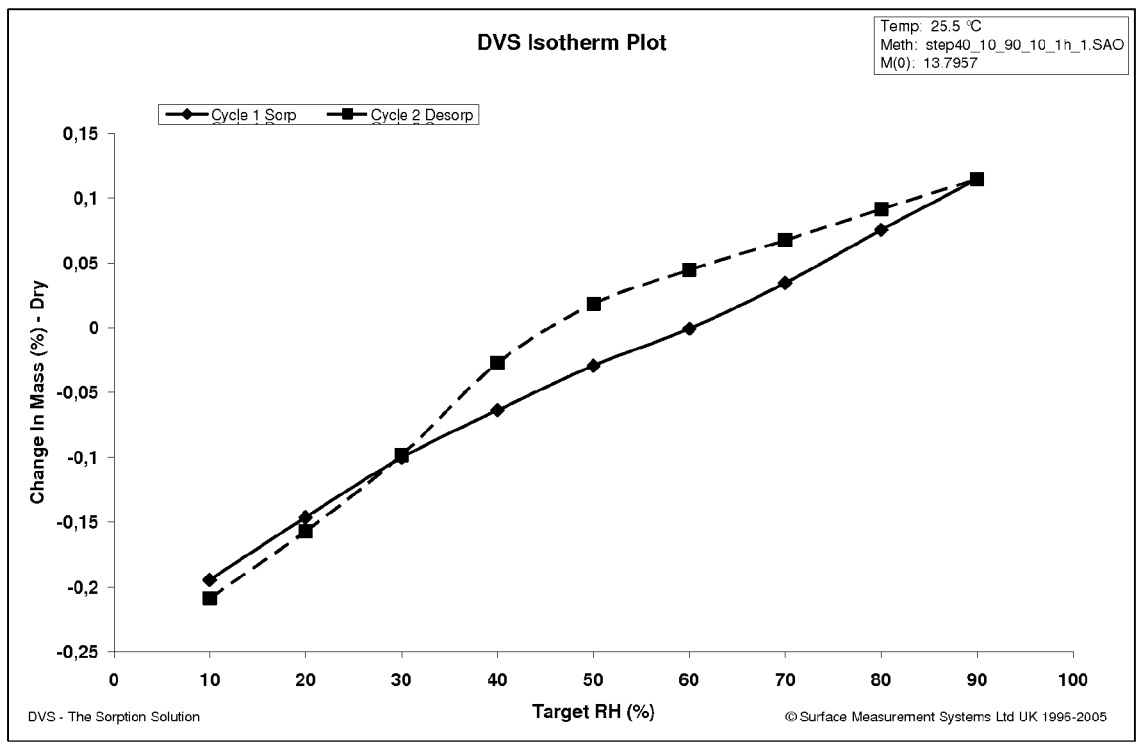

CRYSTALLINE, ENANTIOMERICALLY PURE SALT FORM OF A BETA-AGONIST, AND THE USE THEREOF AS A DRUG

CROSS REFERENCE TO RELATED APPLICATIONS

This application claims priority benefits of DE 08151842.5, filed Feb. 22, 2008; PCT Application No. PCT/EP2009/001082, filed Feb. 17, 2009, respectively, all of which are incorporated by reference herein.

The present invention relates to a crystalline, enantiomerically pure hydrochloride salt of N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide with a melting point of 215° C. and the structure

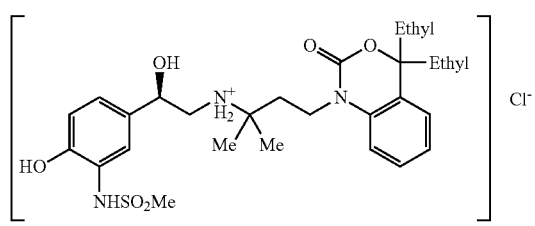

and its activity as a long-acting betamimetic, on its own or in conjunction with one or more other active substances for the treatment of respiratory complaints.

BACKGROUND TO THE INVENTION

Betamimetics (β-adrenergic substances) are known from the prior art. For example reference may be made in this respect to the disclosure of U.S. Pat. No. 4,460,581, which proposes betamimetics for the treatment of a range of diseases.

For drug treatment of diseases it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance at longer time intervals contributes to the well-being of the patient to a high degree.

It is particularly desirable to prepare a pharmaceutical composition which can be used therapeutically by administration once a day (single dose). The use of a drug once a day has the advantage that the patient can become accustomed relatively quickly to regularly taking the drug at certain times of the day.

The enantiomerically pure compound according to formula 1 is a long-acting betamimetic.

Compound 1 used as a medicament for the treatment of respiratory complaints is preferably administered by inhalation. Suitable inhalable powders packed into appropriate capsules (inhalettes) may be administered using corresponding powder inhalers. Alternatively they may be administered by the use of suitable inhalable aerosols. These also include powdered inhalable aerosols which contain, for example, HFA134a, HFA227 or mixtures thereof as propellant gas.

The correct manufacture of the abovementioned compositions which may be used for the administration by inhalation of a pharmaceutical active substance is based on various parameters connected with the nature of the pharmaceutical active substance itself. Without being restricted thereto, examples of these parameters are the stability of effect of the starting material under different ambient conditions, the stability during the manufacture of the pharmaceutical formulation and the stability in the finished compositions of the pharmaceutical substance. The active substance used to prepare the pharmaceutical compositions mentioned above should be as pure as possible, and its stability during long-term storage should be guaranteed under a variety of ambient conditions. This is absolutely essential to prevent the use of pharmaceutical compositions which contain breakdown products of the active substance as well as the active substance itself. In such a case the content of active substance in a capsule might be lower than specified.

The absorption of moisture reduces the content of pharmaceutically active substance on account of the weight gain caused by the uptake of water. Pharmaceutical compositions with a tendency to absorb moisture have to be protected from damp during storage, e.g. By the addition of suitable drying agents or by storing the medicament in a damp-proof environment. In addition, the uptake of moisture can reduce the content of pharmaceutically active substance during manufacture if the medicament is exposed to the environment without being protected from damp in any way.

Uniform distribution of the medicament in the formulation is also a critical factor, particularly when the medicament has to be given in low doses. To ensure uniform distribution, the particle size of the active substance can be reduced to a suitable level, e.g. by grinding. Another aspect which is important in active substances to be administered by inhalation by means of a powder arises from the fact that only particles of a certain size can be taken into the lungs by inhalation. The particle size of these lung-bound particles (inhalable fraction) is in the range between 2 and 5 µm. In order to obtain active substances of a corresponding particle size, a grinding process (so-called micronising) is again required.

Since breakdown of the pharmaceutically active substance as a side effect of the grinding (or micronising) has to be avoided as far as possible, in spite of the hard conditions required during the process, it is absolutely essential that the active substance should be highly stable throughout the grinding process. Only if the active substance is sufficiently stable during the grinding process is it possible to produce a homogeneous pharmaceutical formulation which always contains the specified amount of active substance in reproducible manner.

A specific problem which may arise in the grinding process for preparing the desired pharmaceutical formulation is the input of energy caused by this process and the stress on the surface of the crystals. This may in certain circumstances lead to polymorphous changes, to a change in the amorphous configuration or to a change in the crystal lattice. Since the pharmaceutical quality of a pharmaceutical formulation requires that the active substance should always have the same crystalline morphology, the stability and properties of the crystalline active substance are subject to stringent requirements from this point of view as well.

A particularly important aspect that has to be taken into consideration according to the invention is that, as the specific surface area increases, as happens automatically during micronisation, the surface energy of a particulate system also increases accordingly. As each system tends towards a minimum energy, from the thermodynamic point of view, for particulate systems that have an inhalable particle size and hence a specific surface area of typically between 1 m²/g and 10 m²/g, high demands are made of the crystallinity of the micronised pharmaceutical active substance. It should be noted that crystalline order is thermodynamically preferable to disordered systems and hence crystalline particulate systems are physically more stable from a thermodynamic point of view, particularly when the specific crystal structure is especially stable compared with other crystal structures from a thermodynamic point of view.

The invention therefore sets out in particular to solve the problem of providing a thermodynamically particularly stable form of the compound of formula 1.

BRIEF DESCRIPTION OF THE DRAWINGS

FIG. 1 is an X-ray Powder Diffraction (XRPD) pattern for crystalline compound 1.

FIG. 2 shows the Differential Scanning Calorimetry (DSC)/Thermogravimetric (TG) thermoanalysis curves for crystalline compound 1, where the DSC and TG analyses were performed at a heating rate of 10 K/min in a perforated and open crucible respectively.

FIG. 3 shows the DSV kinetic and isothermic plots for crystalline compound 1.

DETAILED DESCRIPTION OF THE INVENTION

It has now been found that the above-mentioned problems are solved by a crystalline, enantiomerically pure compound of formula 1. The present invention therefore relates to the crystalline, enantiomerically pure compound N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide having the structure:

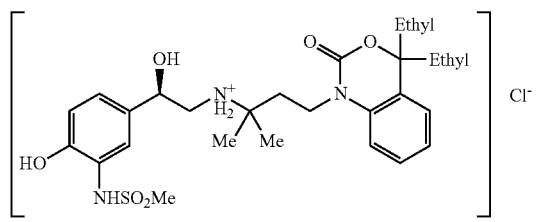

The term enantiomerically pure describes within the scope of the present invention compounds of formula 1 which are present in an enantiomerical purity of at least 85% ee, preferably at least 90% ee, particularly preferably ≧95% ee. The term ee (enantiomeric excess) is known in the art and describes the optical purity of chiral compounds.

The crystalline enantiomerically pure compound 1 may be characterised by a melting point of 215±3° C. Preferably this characterisation is carried out by thermoanalysis (DSC/TG). This new form is further characterised by an X-ray powder diagram (see FIG. 1) with characteristic X-ray reflections according to Table 1.

TABLE 1

Characteristic X-ray diffraction peaks (to 30° 2 Θ) based on standardised intensity data

| 2 Θ [°] | $d_{hkl}$ [Å] | $I/I_o$ | \multicolumn{3}{c}{Indexing} ||| $2\Theta_{obs} - 2\Theta_{calc}$ [°] |
|---|---|---|---|---|---|---|
| | | | h | k | l | |
| 5.77 | 15.30 | 9 | 2 | 0 | 0 | −0.005 |
| 7.25 | 12.19 | 18 | 1 | 1 | 0 | −0.002 |
| 8.81 | 10.03 | 81 | 2 | 1 | 0 | 0.002 |
| 11.57 | 7.64 | 33 | 4 | 0 | 0 | 0.003 |
| 12.90 | 6.86 | 9 | 1 | 0 | 1 | 0.003 |
| 13.85 | 6.39 | 4 | 2 | 0 | 1 | 0.010 |
| 14.22 | 6.22 | 21 | 0 | 1 | 1 | −0.003 |
| 14.52 | 6.10 | 42 | 1 | 1 | 1 | −0.003 |
| 15.37 | 5.76 | 100 | 2 | 1 | 1 | 0.001 |
| 15.94 | 5.56 | 22 | 3 | 2 | 0 | 0.030 |
| 16.69 | 5.31 | 4 | 3 | 1 | 1 | 0.003 |
| 17.39 | 5.09 | 4 | 6 | 0 | 0 | 0.008 |
| 17.67 | 5.02 | 26 | 4 | 2 | 0 | 0.000 |
| 18.38 | 4.82 | 63 | 0 | 2 | 1 | 0.036 |
| 18.56 | 4.78 | 32 | 1 | 2 | 1 | −0.010 |
| 19.25 | 4.61 | 7 | 2 | 2 | 1 | 0.003 |
| 19.70 | 4.50 | 3 | 5 | 2 | 0 | −0.009 |
| 20.35 | 4.36 | 50 | 3 | 2 | 1 | 0.027 |
| 20.86 | 4.26 | 41 | 2 | 3 | 0 | 0.000 |
| 21.50 | 4.13 | 39 | 6 | 0 | 1 | −0.008 |
| 21.74 | 4.09 | 45 | 4 | 2 | 1 | −0.001 |
| 21.95 | 4.05 | 15 | 6 | 2 | 0 | −0.008 |
| 22.53 | 3.94 | 26 | 6 | 1 | 1 | −0.006 |
| 23.44 | 3.79 | 3 | 5 | 2 | 1 | −0.004 |
| 23.89 | 3.72 | 19 | 1 | 3 | 1 | −0.001 |
| 24.36 | 3.65 | 27 | 7 | 2 | 0 | −0.001 |
| 24.88 | 3.58 | 2 | 7 | 1 | 1 | −0.009 |
| 25.39 | 3.51 | 24 | 6 | 2 | 1 | 0.013 |
| 25.95 | 3.43 | 6 | 2 | 0 | 2 | −0.003 |
| 26.15 | 3.40 | 5 | 0 | 1 | 2 | −0.016 |
| 26.82 | 3.32 | 14 | 0 | 4 | 0 | 0.009 |
| 27.53 | 3.24 | 16 | 7 | 2 | 1 | 0.030 |
| 27.89 | 3.20 | 9 | 4 | 0 | 2 | 0.003 |
| 28.68 | 3.11 | 6 | 7 | 3 | 0 | 0.005 |
| 29.22 | 3.05 | 12 | 5 | 0 | 2 | −0.030 |
| 29.97 | 2.98 | 6 | 9 | 1 | 1 | 0.028 |

The crystalline enantiomerically pure compound 1 may be characterised by an X-ray powder diagram with the characteristic X-ray reflections at d=10.03 Å; 5.76 Å; 4.82 Å; 4.36 Å, inter alia. Particularly preferred is a crystalline enantiomerically pure compound 1 with the characteristic X-ray reflections at d=10.03 Å; 6.10 Å; 5.76 Å; 4.82 Å; 4.36 Å; 4.26 Å; 4.13 Å; 4.09 Å; inter alia.

The X-ray powder diagram of the crystalline enantiomerically pure compound 1 can be indexed with the following orthorhombic cell (spatial group $P2_12_12_1$) with the following cell constants: a=30.583 (16) Å, b=13.291 (8) Å, c=7.040 (3) Å, α=β=γ=90°, V=2861.6 (37) Å³ (index value 107.3).

The preferred compound is the crystalline, enantiomerically pure compound 1, characterised in that it is thermally stable at a thermal load of up to 210° C. (cf. FIG. 2).

The greatest weight loss in the TG experiment is observed when the substance is melted (melting with decomposition). The drying loss up to 210° C. includes only water which is freely available on the surface or superficially adsorbed. Starting from these thermal characteristics in the TG experiment, it is possible to draw conclusions as to the stoichiometry of the crystalline compound, which is consequently not present in the form of the solvate or hydrate.

The crystalline, enantiomerically pure compound 1 is further characterised by the following water absorption characteristics: In the relative humidity range between 10-90% n.h., compound 1 absorbs less than 0.5 wt. % water.

The present invention further relates to pharmaceutical compositions, characterised in that they contain the crystalline, enantiomerically pure compound 1 according to the invention. These compositions are preferably used to treat respiratory complaints. The present invention further relates to the use of the crystalline, enantiomerically pure compound 1 for preparing a pharmaceutical composition for the treatment of respiratory complaints.

The present invention preferably relates to the use of the above-mentioned crystalline and enantiomerically pure compounds of formula 1 for preparing a pharmaceutical composition for the treatment of respiratory complaints, selected from among obstructive pulmonary diseases of various origins, pulmonary emphysema of various origins, restrictive pulmonary diseases, interstitial pulmonary diseases, cystic fibrosis, bronchitis of various origins, bronchiectasis, ARDS (adult respiratory distress syndrome) and all forms of pulmonary oedema.

Indications

Preferably the crystalline and enantiomerically pure compound of formula 1 is used to prepare a pharmaceutical composition for the treatment of obstructive pulmonary diseases selected from among COPD (chronic obstructive pulmonary disease), bronchial asthma, paediatric asthma, severe asthma, acute asthma attacks, and chronic bronchitis, while it is particularly preferable according to the invention to use it to prepare a medicament for the treatment of bronchial asthma.

It is also preferable to use the crystalline and enantiomerically pure compound of formula 1 for preparing a pharmaceutical composition for the treatment of pulmonary emphysema which has its origins in COPD (chronic obstructive pulmonary disease) or α1-proteinase inhibitor deficiency.

It is also preferable to use the crystalline and enantiomerically pure compound of formula 1 for preparing a pharmaceutical composition for the treatment of restrictive pulmonary diseases selected from among allergic alveolitis, restrictive pulmonary diseases triggered by work-related noxious substances, such as asbestosis or silicosis, and restriction caused by lung tumours, such as for example lymphangiosis carcinomatosa, bronchoalveolar carcinoma and lymphomas.

It is also preferable to use the crystalline and enantiomerically pure compound of formula 1 for preparing a pharmaceutical composition for the treatment of interstitial pulmonary diseases selected from among pneumonia caused by infections, such as for example infection by viruses, bacteria, fungi, protozoa, helminths or other pathogens, pneumonitis caused by various factors, such as for example aspiration and left heart insufficiency, radiation-induced pneumonitis or fibrosis, collagenoses, such as for example lupus erythematodes, systemic sclerodermy or sarcoidosis, granulomatoses, such as for example Boeck's disease, idiopathic interstitial pneumonia or idiopathic pulmonary fibrosis (IPF).

It is also preferable to use the crystalline and enantiomerically pure compound of formula 1 for preparing a pharmaceutical composition for the treatment of cystic fibrosis or mucoviscidosis.

It is also preferable to use the crystalline and enantiomerically pure compound of formula 1 for preparing a pharmaceutical composition for the treatment of bronchitis, such as for example bronchitis caused by bacterial or viral infection, allergic bronchitis and toxic bronchitis.

It is also preferable to use the crystalline and enantiomerically pure compound of formula 1 for preparing a pharmaceutical composition for the treatment of bronchiectasis.

It is also preferable to use the crystalline and enantiomerically pure compound of formula 1 for preparing a pharmaceutical composition for the treatment of ARDS (adult respiratory distress syndrome).

It is also preferable to use the crystalline and enantiomerically pure compound of formula 1 for preparing a pharmaceutical composition for the treatment of pulmonary oedema, for example toxic pulmonary oedema after aspiration or inhalation of toxic substances and foreign substances.

Particularly preferably, the present invention relates to the use of the crystalline and enantiomerically pure compound of formula 1 for preparing a pharmaceutical composition for the treatment of asthma or COPD. Also of particular importance is the above-mentioned use for preparing a pharmaceutical composition for once-a-day treatment of inflammatory and obstructive respiratory complaints, particularly for the once-a-day treatment of asthma or COPD.

In addition, the present invention relates to a method of treating the above-mentioned diseases, characterised in that one or more of the above-mentioned crystalline and enantiomerically pure compound of formula 1 are administered in therapeutically effective amounts. The present invention preferably relates to methods of treating asthma or COPD, characterised in that the above-mentioned crystalline and enantiomerically pure compound of formula 1 are administered once a day in therapeutically effective amounts.

Medicament compositions that are suitable for administration are those which contain the crystalline enantiomerically pure compound 1 in an inhalable solution or in a powder formulation suitable for administration by inhalation. Also suitable are medicament compositions which contain the crystalline, enantiomerically pure compound 1 according to the invention and another active substance, one or more compounds selected from among the categories of the anticholinergics, corticosteroids, PDE4-inhibitors, LTD4-antagonists, EGFR-inhibitors, dopamine agonists, H1-antihistamines and PI3-kinase inhibitors or double or triple combinations thereof.

Moreover the present invention relates to a method of treating the above-mentioned diseases, characterised in that the above-mentioned crystalline enantiomerically pure compound of formula 1 are administered in therapeutically effective amounts. The present invention preferably relates to methods of treating asthma or COPD, characterised in that the above-mentioned crystalline, enantiomerically pure compound of formula 1 is administered once a day in therapeutically effective amounts.

Suitable formulations for administering the crystalline enantiomerically pure compound of formula 1 include for example tablets, capsules, suppositories, powders etc. The content of the pharmaceutically active compound should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

In the particularly preferred use of the crystalline and enantiomerically pure compound of formula 1 for the treatment of respiratory complaints it is particularly preferred according to the invention to use preparations or pharmaceutical formulations which can be administered by inhalation. Inhalable preparations include inhalable powders and propellant-containing metered-dose aerosols.

The compound of formula 1 which is particularly preferably used in crystalline enantiomerically pure form according to the invention is preferably used to prepare powders for inhalation. The inhalable powders which may be used according to the invention may contain the crystalline enantiomerically pure compound of formula 1 either on its own or in admixture with suitable physiologically acceptable excipients.

If the active substances are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 and 150 µm, most preferably between 15 and 80 µm. In some cases it may seem appropriate to add finer excipient fractions with an average particle size of 1 to 9 µm to the excipients mentioned above. These finer excipients are also selected from the group of possible excipients listed hereinbefore. Finally, in order to prepare the inhalable powders according to the invention, micronised active substance, preferably with an average particle size of 0.5 to 10 µm, more preferably from 1 to 5 µm, is added to the excipient mixture. Processes for producing the inhalable powders according to the invention by grinding and micronising and finally mixing the ingredients together are known from the prior art.

The inhalable powders according to the invention may be administered using inhalers known from the prior art.

Inhalation aerosols containing propellant gas according to the invention may contain the crystalline enantiomerically pure compounds 1 in dispersed form in the propellant gas. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The above-mentioned propellant gases may be used on their own or in admixture. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols mentioned above may be administered using inhalers known in the art (MDIs=metered dose inhalers).

The dosage of the compounds according to the invention is naturally highly dependent on the method of administration and the complaint which is being treated. When administered by inhalation the compounds of the formula are characterised by a high potency even at doses in the µg range. The compounds of the formula may also be used effectively above the µg range. The dosage may then be in the milligram range, for example.

In another aspect the present invention relates to the abovementioned pharmaceutical formulations as such, which are characterised in that they contain a compound of formula 1 as such, particularly preferably the above-mentioned pharmaceutical formulations administered by inhalation.

The following examples of formulations illustrate the present invention without restricting its scope:

A)

| Tablets | per tablet |
| --- | --- |
| active substance | 100 mg |
| lactose | 140 mg |
| corn starch | 240 mg |
| polyvinylpyrrolidone | 15 mg |
| magnesium stearate | 5 mg |
|  | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B)

| Tablets | per tablet |
| --- | --- |
| active substance | 80 mg |
| corn starch | 190 mg |
| lactose | 55 mg |
| microcrystalline cellulose | 35 mg |
| polyvinylpyrrolidone | 15 mg |
| sodium-carboxymethyl starch | 23 mg |
| magnesium stearate | 2 mg |
|  | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

C)

| Metering aerosol | |
|---|---|
| active substance 1 | 0.005 |
| sorbitan trioleate | 0.1 |
| TG134a:TG227 2:1 | ad 100 |

The suspension is transferred into a conventional aerosol container with metering valve. Preferably 50 μl suspension are released on each actuation. The active substance may also be released in higher doses if desired (e.g. 0.02 wt.-%).

D)

| Inhalable powder | |
|---|---|
| active substance | 12 μg |
| lactose monohydrate | ad 10 mg |

The inhalable powder is prepared in the conventional manner by mixing the individual constituents.

E)

| Solutions (in mg/100 ml) | |
|---|---|
| active substance | 333.3 mg |
| benzalkonium chloride | 10.0 mg |
| EDTA | 50.0 mg |
| HCl (1n) | ad pH 3.4 |

This solution may be prepared in the conventional manner.

F)

| Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilised and heat-sealed. The ampoules contain 5 mg, 25 mg and 50 mg of active substance.

EXPERIMENTAL SECTION

Compound 2 in the form of its base is known from WO-A-2007/054484:

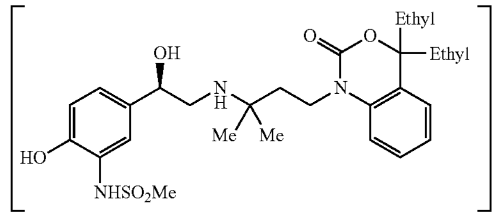

2

Regarding the synthesis of 2 reference is hereby made to Example 1d from WO-A-2007/054484 in connection with the synthesis described in WO-A-2007/054484 for preparing the optically pure R-enantiomer N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide according to formula 2.

Preparation According to the Invention of the Crystalline, Enantiomerically Pure Compound 1 with a Melting Point of 215° C.

Example 1

30 g of compound 2 are suspended in 345 mL acetonitrile and 16.5 mL water.

At 16-18° C., 6.8 g 30% hydrochloric acid are carefully added, followed by a further 45 mL acetonitrile. The solution is heated to 65° C., activated charcoal is added and the mixture is filtered. The filter cake is washed with 105 mL acetonitrile and the filtrate is refluxed. The solution is evaporated down by distillation, during which time 1 crystallises out. A further 180 mL acetonitrile are added and the distillation is continued. As soon as 250 mL of the solvent has been distilled off, the suspension is cooled to 10° C. and the crystals precipitated are filtered off and washed with 2×60 mL cold acetonitrile. Then the crystals are dried at 50° C. The yield is 29 g (91%).

Example 2

50 g of compound 2 are suspended in 575 mL n-butyl-alcohol. 6.8 g of 30% hydrochloric acid are carefully added to this suspension at ambient temperature, followed by another 20 mL water and a further 75 mL n-butyl-alcohol. The remaining suspension is heated to 80° C. and the solution thus formed is filtered off through activated charcoal. The filter cake is washed with another 225 mL of n-butyl-alcohol. Some of the solvent is distilled off at this temperature, while at the same time a weak vacuum is applied. During this time, some crystallisation of 1 is observed. After 150 mL of the solvent has been eliminated the remaining suspension is cooled to 10° C. and the crystals precipitated are filtered off and washed with 2×100 mL cold n-butyl-alcohol. Then the crystals are dried at 50° C. The yield is 45 g (84%).

Alternatively the compound 1 according to the invention may also be prepared as follows:

Example 3

2.05 mmol of the free base of the compound of formula 2 are suspended in 7 mL acetone and combined with 506 μl (2.02 mmol) 4 molar hydrochloric acid in 550 μl acetone, whereupon a clear solution is formed. After the addition of a crystallisation aid a total of 7 mL of diethyl ether are added dropwise. The precipitated solid is separated off after 3 hours, washed with diethyl ether and dried at 40° C. Then the solid is recrystallised from acetonitrile with the addition of a few drops of water, filtered and washed again with diethyl ether. Yield: 46%, melting point: 162±3° C.

500 mg of this intermediate is dissolved in 5 ml acetonitrile and 0.2 mL water at 60° C. The precipitation of the crystals is induced by the addition of crystals as may be obtained for example in Example 1 or Example 2. The mixture is cooled to ambient temperature and stirred for a further 4 hours at this temperature. The crystals precipitated are filtered off, washed with 1 mL acetonitrile 2×1 mL butylmethylether and dried at 40° C. The yield of the compound according to formula 1 is 460 mg (92%).

Example 4

2.05 mmol of the free base of the compound of formula 2 are suspended in 7 mL acetone and combined with 506 µl (2.02 mmol) 4 molar hydrochloric acid in 550 µl acetone, whereupon a clear solution is formed. After the addition of a crystallisation aid a total of 7 mL diethyl ether are added dropwise. The precipitated solid is separated off after 3 hours, washed with diethyl ether and dried at 40° C. Then the solid is recrystallised from acetonitrile with the addition of a few drops of water, filtered and washed again with diethyl ether. Yield: 46%, melting point: 162±3° C.

500 mg of this intermediate is suspended in 5 mL acetonitrile (0.05 mL water may optionally be added to this suspension) and the mixture is stirred for 20 hours at 40° C.

Then the mixture is cooled to ambient temperature. The crystals precipitated are filtered off, washed with 1 mL acetonitrile 2×1 mL butylmethylether and dried at 40° C. The yield of the compound according to formula 1 is 480 mg (96%).

X-Ray Powder Diagram (FIG. 1)
Parameters of the X-Ray Powder Diffractometer Used for the Measurement:

STOE Stadi P X-ray powder diffractometer with a location-sensitive detector in transmission mode with a curved germanium (111) primary monochromator; wavelength used: $CuK_{\alpha 1}$ with $\lambda$=1.540598 Å; power capacity of the X-ray tube: 40 kV, 40 mA; recording range: 3-40°2Θ.

The TREOR software (part of the STOE Stadi P software package) was used to indicate the peaks in the X-ray powder diagram.
Thermoanalysis (DSC/TG Diagram, FIG. 2)
Technical Data Relating to the Thermoanalytical DSC Device Used:

DSC 822 made by Mettler Toledo; heating rate: 10 K/min; type of crucible: perforated aluminium crucible; atmosphere: $N_2$, 80 ml/min flux; weight: 3-10 mg.
Technical Data Relating to the Thermoanalytical TG Device Used:

TGA/SDTA 851 Made by Mettler Toledo with IR coupling (Nicolet FT-IR 4700) for analysing the volatile fractions driven off; heating rate: 10 K/min; type of crucible: open aluminium oxide crucible; atmosphere: $N_2$, 20 ml/min flux; weight: 15-25 mg.
Sorption Profile (DSV Diagram, Kinetic & Isothermic Plot, FIG. 3)
Technical Data Relating to the Sorption Balance Used:

DVS-1 made by Surface Measurement Systems (=SMS) for analysing the hygroscopic characteristics; humidity profile of 10-90% r.h. In 10% steps, recording both a sorption and a desorption profile, weight: 10-20 mg
Combinations The crystalline and enantiomerically pure compound of formula 1 may be used on its own or in combination with other active substances. If desired the crystalline and enantiomerically pure compound of formula 1 may also be used in combination with W, where W denotes a pharmacologically active substance and (for example) is selected from among the anticholinergics, corticosteroids, PDE4-inhibitors, LTD4-antagonists, EGFR-inhibitors, dopamine agonists, H1-antihistamines and PI3-kinase inhibitors. Moreover, double or triple combinations of W may be combined with the crystalline and enantiomerically pure compound of formula 1. Combinations of W might be, for example:

W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, aclidinium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred. Other specified compounds are tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide; tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide; tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenyl-propionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, cyclopropyltropine methyl 4,4'-difluorobenzilate methobromide, tropenol 9-hydroxy-xanthene-9-carboxylate methobromide, scopine 9-hydroxy-xanthene-9-carboxylate methobromide, tropenol 9-methyl-xanthene-9-carboxylate-methobromide, scopine 9-methyl-xanthene-9-carboxylate-methobromide, tropenol 9-ethyl-xanthene-9-carboxylate methobromide, tropenol 9-difluoromethyl-xanthene-9-carboxylate methobromide, scopine 9-hydroxymethyl-xanthene-9-carboxylate methobromide.

Compounds which may be used as corticosteroids are preferably those selected from among prednisolone, prednisone, butixocort, flunisolide, beclomethasone, triamcinolone, budesonide, fluticasone, mometasone, ciclesonide, rofleponide, dexamethasone, betamethasone, deflazacort, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothionate; (S)-(2-oxo-tetrahydro-furan-3S-yl) 6,9-difluoro-11-hydroxy-16-methyl-3-oxo-17-propionyloxy-androsta-1,4-dien-17-carbothionate; etiprednol-dichloroacetate, optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof that may exist. Examples of possible salts and derivatives of the steroids may be: alkali metal salts, such as for example sodium or potassium salts, sulphobenzoates, phosphates, isonicotinates, acetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and N-(3,5-dichloro-1-oxo-pyridin-4-yl)-4-difluoromethoxy-3-cyclopropylmethoxy-benzamide; (−)p-[(4aR*,10bS*)-9-ethoxy-1,2,3,4,4a,10b-hexahydro-8-methoxy-2-methylbenzo[s][1.6]naphthyridin-6-yl]-N,N-diisopropylbenzamide; (R)-(+)-1-(4-bromobenzyl)-4-[(3-cyclopentyloxy)-4-methoxyphenyl]-2-pyrrolidone; 3-(cyclopentyloxy-4-methoxyphenyl)-1-(4-N'-[N-2-cyano-S-methyl-isothioureido]benzyl)-2-pyrrolidone; cis[4-cyano-4-(3-cyclopentyloxy-4-methoxyphenyl)cyclohexane-1-carboxylic acid]; 2-carbomethoxy-4-cyano-4-(3-cyclopropylmethoxy-4-difluoromethoxy-phenyl)cyclohexan-1-one; cis[4-cyano-4-(3-cyclopropylmethoxy-4-difluoromethoxyphenyl)cyclohexan-1-ol]; (R)-(+)-ethyl[4-(3-cyclopentyloxy-4-methoxyphenyl)pyrrolidin-2-ylidene]acetate; (S)-(−)-ethyl[4-(3-cyclopentyloxy-4-methoxyphenyl)pyrrolidin-2-ylidene]acetate; 9-cyclopentyl-5,6-dihydro-7-ethyl-3-(2-thienyl)-9H-pyrazolo[3,4-c]-1,2,4-triazolo[4.3-a]pyridine; 9-cyclopentyl-5,6-dihydro-7-ethyl-3-(tert-butyl)-9H-pyrazolo[3,4-c]-1,2,4-triazolo[4.3-a]pyridine, optionally in the form of the racemates, enantiomers, diastereomers thereof and optionally in the form of the pharmacologically acceptable acid addition salts, solvates or hydrates thereof. Preferred, according to the invention, are the acid addition salts of the betamimetics selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of LTD4-antagonists used here are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid; 1-(((1R)-3-(3-(2-(2,3-dichlorothieno[3.2-b]pyridin-5-yl)-(E)-ethenyl)phenyl)-3-(2-(1-hydroxy-1-methylethyl)phenyl)propyl)thio)methyl)cyclopropane-acetic acid; [2-[[2-(4-tert-butyl-2-thiazolyl)-5-benzofuranyl]oxymethyl]phenyl]acetic acid, optionally in the form of the racemates, enantiomers, diastereomers thereof and optionally in the form of the pharmacologically acceptable acid addition salts, solvates or hydrates thereof.

Preferred, according to the invention, are the acid addition salts of the betamimetics selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

Examples of EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]amino}-7-cyclopropylmethoxy-quinazoline; 4-[(3-chloro-4-fluorophenyl)amino]-6-{[4-(N,N-diethylamino)-1-oxo-2-buten-1-yl]amino}-7-cyclopropylmethoxy-quinazoline; 4-[(3-chloro-4-fluorophenyl)amino]-6-{[4-(N,N-dimethylamino)-1-oxo-2-buten-1-yl]amino}-7-cyclopropylmethoxy-quinazoline; 4-[(R)-(1-phenyl-ethyl)amino]-6-{[4-(morpholin-4-yl)-1-oxo-2-buten-1-yl]amino}-7-cyclopentyloxy-quinazoline; 4-[(3-chloro-4-fluoro-phenyl)amino]-6-{[4-(R)-6-methyl-2-oxo-morpholin-4-yl)-1-oxo-2-buten-1-yl]amino}-7-cyclopropylmethoxy-quinazoline; 4-[(3-chloro-4-fluorophenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline; 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline; 4-[(3-chloro-4-fluoro-phenyl)amino]-6-[2-((S)-6-methyl-2-oxo-morpholin-4-yl)-ethoxy]-7-methoxy-quinazoline; 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline; 4-[(3-chloro-4-fluorophenyl)amino]-6-{[4-(N,N-dimethylamino)-1-oxo-2-buten-1-yl]amino}-7-cyclopentyloxy-quinazoline; 4-[(R)-(1-phenyl-ethyl)amino]-6-{[4-(N,N-bis-(2-methoxy-ethyl)-amino)-1-oxo-2-buten-1-yl]amino}-7-cyclopropyl-methoxy-quinazoline; 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline; 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline; 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline; 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline; 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline; 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline; 4-[(3-chloro-4-fluorophenyl)amino]-6-{[4-(N-cyclopropyl-N-methyl-amino)-1-oxo-2-buten-1-yl]amino}-7-cyclopentyloxy-quinazoline; 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline; 4-[(3-chloro-4-fluorophenyl)amino]-6-{[4-(N,N-dimethylamino)-1-oxo- 2-buten-1-yl]amino}-7-[(S)-(tetrahydrofuran-2-yl)methoxy]-quinazoline; 4-[(3-ethynyl-phenyl)amino]-6.7-bis-(2-methoxy-ethoxy)-quinazoline; 4-[(3-chloro-4-fluorophenyl)amino]-7-[3-(morpholin-4-yl)-propyloxy]-6-[(vinylcarbonyl)amino]-quinazoline; 4-[(R)-(1-phenyl-ethyl)amino]-6-(4-hydroxy-phenyl)-7H-pyrrolo[2,3-d]pyrimidine; 3-cyano-4-[(3-chloro-4-fluorophenyl)amino]-6-{[4-(N,N-dimethylamino)-1-oxo-2-buten-1-yl]amino}-7-ethoxy-quinoline; 4-{[3-chloro-4-(3-fluoro-benzyloxy)-phenyl]amino}-6-(5-{[(2-methanesulphonyl-ethyl)amino]methyl}-furan-2-yl)quinazoline; 4-[(R)-(1-phenyl-ethyl)amino]-6-{[4-(R)-6-methyl-2-oxo-morpholin-4-yl)-1-oxo-2-buten-1-yl]amino}-7-methoxy-quinazoline; 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline; 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline; 4-[(3-ethynyl-phenyl)amino]-6-{[4-(5.5-dimethyl-2-oxo-morpholin-4-yl)-1-oxo-2-buten-1-yl]amino}-quinazoline; 4-[(3-chloro-4-fluoro-phenyl)amino]-6-[2-(2,2-dimethyl-6-oxo-morpholin-4-yl)-ethoxy]-7-methoxy-quinazoline; 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline; 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline; 4-[(3-chloro-4-fluoro-phenyl)amino]-6-{2-[4-(2-oxo-morpholin-4-yl)-piperidin-1-yl]-ethoxy}-7-methoxy-quinazoline; 4-[(3-chloro-4-fluoro-phenyl)amino]-6-[1-(tert.-butyloxycarbonyl)-piperidin-4-yloxy]-7-methoxy-quinazoline; 4-[(3-chloro-4-fluoro-phenyl)amino]-6-(trans-4-amino-cyclohexan-1-yloxy)-7-methoxy-quinazoline; 4-[(3-chloro-4-fluoro-phenyl)amino]-6-(trans-4-methanesulphonylamino-cyclohexan-1-yloxy)-7-methoxy-quinazoline; 4-[(3-chloro-4-fluoro-phenyl)amino]-6-(tetrahydropyran-3-yloxy)-7-methoxy-quinazoline; 4-[(3-chloro-4-fluoro-phenyl)amino]-6-(1-methyl-piperidin-4-yloxy)-7-methoxy-quinazoline; 4-[(3-chloro-4-fluoro-phenyl)amino]-6-{1-[(morpholin-4-yl)carbonyl]-piperidin-4-yloxy}-7-methoxy-quinazoline; 4-[(3-chloro-4-fluoro-phenyl)amino]-6-{1-[(methoxymethyl)carbonyl]-piperidin-4-yloxy}-7-methoxy-quinazoline; 4-[(3-chloro-4-fluoro-phenyl)amino]-6-(piperidin-3-yloxy)-7-methoxy-quinazoline; 4-[(3-chloro-4-fluoro-phenyl)amino]-6-[1-(2-acetylamino-ethyl)-piperidin-4-yloxy]-7-methoxy-quinazoline; 4-[(3-chloro-4-fluoro-phenyl)amino]-6-(tetrahydropyran-4-yloxy)-7-ethoxy-quinazoline; 4-[(3-chloro-4-fluoro-phenyl)amino]-6-((S)-tetrahydrofuran-3-yloxy)-7-hydroxy-quinazoline; 4-[(3-chloro-4-fluoro-phenyl)amino]-6-(tetrahydropyran-4-yloxy)-7-(2-methoxy-ethoxy)-quinazoline; 4-[(3-chloro-4-fluoro-phenyl)amino]-6-{trans-4-[(dimethylamino)sulphonylamino]-cyclohexan-1-yloxy}-7-methoxy-quinazoline; 4-[(3-chloro-4-fluoro-phenyl)amino]-6-{trans-4-[(morpholin-4-yl)carbonylamino]-cyclohexan-1-yloxy}-7-methoxy-quinazoline; 4-[(3-chloro-4-fluoro-phenyl)amino]-6-{trans-4-[(morpholin-4-yl)sulphonylamino]-cyclohexan-1-yloxy}-7-methoxy-quinazoline; 4-[(3-chloro-4-fluoro-phenyl)amino]-6-(tetrahydropyran-4-yloxy)-7-(2-acetylamino-ethoxy)-quinazoline; 4-[(3-chloro-4-fluoro-phenyl)amino]-6-(tetrahydropyran-4-yloxy)-7-(2-methanesulphonylamino-ethoxy)-quinazoline; 4-[(3-chloro-4-fluoro-phenyl)amino]-6-{1-[(piperidin-1-yl)carbonyl]-piperidin-4-yloxy}-7-methoxy-quinazoline; 4-[(3-chloro-4-fluoro-phenyl)amino]-6-(1-aminocarbonylmethyl-piperidin-4-yloxy)-7-methoxy-quinazoline; 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline; 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline; 4-[(3-chloro-4-fluoro-phenyl)amino]-6-(cis-4-{N-[(morpholin-4-yl) sulphonyl]-N-methyl-amino}-cyclohexan-1-yloxy)-7-methoxy-quinazoline; 4-[(3-chloro-4-fluoro-phenyl)amino]-6-(trans-4-ethanesulphonylamino-cyclohexan-1-yloxy)-7-methoxy-quinazoline; 4-[(3-chloro-4-fluoro-phenyl)amino]-6-(1-methanesulphonyl-piperidin-4-yloxy)-7-ethoxy-quinazoline; 4-[(3-chloro-4-fluoro-phenyl)amino]-6-(1-methanesulphonyl-piperidin-4-yloxy)-7-(2-methoxy-ethoxy)-quinazoline; 4-[(3-chloro-4-fluoro-phenyl)amino]-6-[1-(2-methoxy-acetyl)-piperidin-4-yloxy]-7-(2-methoxy-ethoxy)-quinazoline; 4-[(3-chloro-4-fluoro-phenyl)amino]-6-(cis-4-acetylamino-cyclohexan-1-yloxy)-7-methoxy-quinazoline; 4-[(3-ethynyl-phenyl)amino]-6-[1-(tert.-butyloxycarbonyl)-piperidin-4-yloxy]-7-methoxy-quinazoline; 4-[(3-ethynyl-phenyl)amino]-6-(tetrahydropyran-4-yloxy)-7-methoxy-quinazoline; 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline; 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline; 4-[(3-chloro-4-fluoro-phenyl)amino]-6-{cis-4-[(morpholin-4-yl)carbonylamino]-cyclohexan-1-yloxy}-7-methoxy-quinazoline; 4-[(3-chloro-4-fluoro-phenyl)amino]-6-{1-[2-(2-oxopyrrolidin-1-yl)ethyl]-piperidin-4-yloxy}-7-methoxy-quinazoline; 4-[(3-chloro-4-fluoro-phenyl)amino]-6-{1-[(morpholin-4-yl)carbonyl]-piperidin-4-yloxy}-7-(2-methoxy-ethoxy)-quinazoline; 4-[(3-ethynyl-phenyl)amino]-6-(1-acetyl-piperidin-4-yloxy)-7-methoxy-quinazoline; 4-[(3-ethynyl-phenyl)amino]-6-(1-methyl-piperidin-4-yloxy)-7-methoxy-quinazoline; 4-[(3-ethynyl-phenyl)amino]-6-(1-methanesulphonyl-piperidin-4-yloxy)-7-methoxy-quinazoline; 4-[(3-chloro-4-fluoro-phenyl)amino]-6-(1-methyl-piperidin-4-yloxy)-7-(2-methoxy-ethoxy)-quinazoline; 4-[(3-chloro-4-fluoro-phenyl)amino]-6-(1-isopropyloxycarbonyl-piperidin-4-yloxy)-7-methoxy-quinazoline; 4-[(3-chloro-4-fluoro-phenyl)amino]-6-(cis-4-methylamino-cyclohexan-1-yloxy)-7-methoxy-quinazoline; 4-[(3-chloro-4-fluoro-phenyl)amino]-6-{cis-4-[N-(2-methoxy-acetyl)-N-methyl-amino]-cyclohexan-1-yloxy}-7-methoxy-quinazoline; 4-[(3-ethynyl-phenyl)amino]-6-(piperidin-4-yloxy)-7-methoxy-quinazoline; 4-[(3-ethynyl-phenyl)amino]-6-[1-(2-methoxy-acetyl)-piperidin-4-yloxy]-7-methoxy-quinazoline; 4-[(3-ethynyl-phenyl)amino]-6-{1-[(morpholin-4-yl)carbonyl]-piperidin-4-yloxy}-7-methoxy-quinazoline; 4-[(3-chloro-4-fluoro-phenyl)amino]-6-{1-[(cis-2,6-dimethyl-morpholin-4-yl)carbonyl]-piperidin-4-yloxy}-7-methoxy-quinazoline; 4-[(3-chloro-4-fluoro-phenyl)amino]-6-{1-[(2-methyl-morpholin-4-yl)carbonyl]-piperidin-4-yloxy}-7-methoxy-quinazoline; 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline; 4-[(3-chloro-4-fluoro-phenyl)amino]-6-{1-[(N-methyl-N-2-methoxyethyl-amino)carbonyl]-piperidin-4-yloxy}-7-methoxy-quinazoline; 4-[(3-chloro-4-fluoro-phenyl)amino]-6-(1-ethyl-piperidin-4-yloxy)-7-methoxy-quinazoline; 4-[(3-chloro-4-fluoro-phenyl)amino]-6-{1-[(2-methoxyethyl)carbonyl]-piperidin-4-yloxy}-7-methoxy-quinazoline; 4-[(3-chloro-4-fluoro-phenyl)amino]-6-{1-[(3-methoxypropyl-amino)-carbonyl]-piperidin-4-yloxy}-7-methoxy-quinazoline; 4-[(3-chloro-4-fluoro-phenyl)amino]-6-[cis-4-(N-methanesulphonyl-N-methyl-amino)-cyclohexan-1-yloxy]-7-methoxy-quinazoline; 4-[(3-chloro-4-fluoro-phenyl)amino]-6-[cis-4-(N-acetyl-N-methylamino)-cyclohexan-1-yloxy]-7-methoxy-quinazoline; 4-[(3-chloro-4-fluoro-phenyl)amino]-6-(trans-4-methylamino-cyclohexan-1-yloxy)-7-methoxy-quinazoline; 4-[(3-chloro-4-fluoro-phenyl)amino]-6-[trans-4-(N-methanesulphonyl-N-methyl-amino)-cyclohexan-1-yloxy]-7-methoxy-quinazoline; 4-[(3-chloro-4-fluoro-phenyl)amino]-6-(trans-4-dimethylamino-cyclohexan-1-yloxy)-7-methoxy-quinazoline; 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline; 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline; 4-[(3-chloro-4-fluoro-phenyl)amino]-6-(1-methanesulphonyl-piperidin-4-yloxy)-7-methoxy-quinazoline; 4-[(3-chloro-4-fluoro-phenyl)amino]-6-(1-cyano-piperidin-4-yloxy)-7-methoxy-quinazoline, optionally in the form of the racemates, enantiomers, diastereomers thereof and optionally in the form of the pharmacologically acceptable acid addition salts, solvates or hydrates thereof. Preferred, according to the invention, are the acid addition salts of the betamimetics selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of dopamine agonists which may be used here are preferably compounds selected from among bromocriptin, cabergolin, alpha-dihydroergocryptin, lisuride, pergolide, pramipexol, roxindol, ropinirol, talipexol, terguride and viozan, optionally in the form of the racemates, enantiomers, diastereomers thereof and optionally in the form of the pharmacologically acceptable acid addition salts, solvates or hydrates thereof. Preferred, according to the invention, are the acid addition salts of the betamimetics selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of H1-antihistamines which may be used here are preferably compounds selected from among epinastine, cetirizine, azelastine, fexofenadine, levocabastine, loratadine, mizolastine, ketotifen, emedastine, dimetinden, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. Preferred, according to the invention, are the acid addition salts of the betamimetics selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The invention claimed is:

1. A crystalline hydrochloride salt of N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide of structure 1

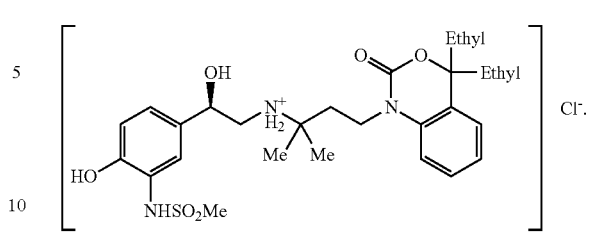

characterized in that it has X-ray reflections at d=10.03 Å; 5.76 Å; 4.82 Å; 4.36 Å.

2. A crystalline hydrochloride salt of structure 1 characterised in that it melts at 215±3° C. with decomposition.

3. A crystalline hydrochloride salt of structure 1 according to claim 1, characterised in that it has X-ray reflections at d=10.03 Å; 6.10 Å; 5.76 Å; 4.82 Å; 4.36 Å; 4.26 Å; 4.13 Å; 4.09 Å.

4. A crystalline hydrochloride salt of structure 1 according to claim 1, characterised in that its crystal structure has a single orthorhombic cell (spatial group $P2_12_12_1$) with the following cell constants: a=30.58±0.05 (16) Å, b=13.29±0.05 (8) Å, c=7.04±0.05 (3) Å, $\alpha=\beta=\gamma=90°$, V=2862±5 (37) Å$^3$.

5. A pharmaceutical composition, comprising a crystalline hydrochloride salt of structure 1 according to claim 1 and a pharmaceutically acceptable excipient or carrier.

6. A method for the treatment of respiratory complaints selected from
   obstructive pulmonary diseases selected from among COPD (chronic obstructive pulmonary disease), bronchial asthma, pediatric asthma, severe asthma, acute asthma attacks, chronic bronchitis; pulmonary emphysema which has its origins in COPD (chronic obstructive pulmonary disease) or α1-proteinase inhibitor deficiency;
   restrictive pulmonary diseases selected from among allergic alveolitis, restrictive pulmonary diseases triggered by work-related noxious substances, selected from asbestosis or silicosis, and restriction caused by lung tumours, selected from lymphangiosis carcinomatosa, bronchoalveolar carcinoma and lymphomas;
   interstitial pulmonary diseases selected from among pneumonia caused by infection by viruses, bacteria, fungi, protozoa or helminths, pneumonitis caused by aspiration and left heart insufficiency, radiation-induced pneumonitis or fibrosis, collagenoses, selected from lupus erythematodes, systemic sclerodermy or sarcoidosis, and granulomatoses, selected from Boeck's disease, idiopathic interstitial pneumonia and idiopathic pulmonary fibrosis (IPF);
   comprising administering to a patient in need thereof a therapeutically effective amount of the crystalline hydrochloride salt of structure 1 according to claim 1 in an inhalable solution.

7. A method for the treatment of respiratory complaints selected from
   obstructive pulmonary diseases selected from among COPD (chronic obstructive pulmonary disease), bronchial asthma, pediatric asthma, severe asthma, acute asthma attacks, chronic bronchitis; pulmonary emphysema which has its origins in COPD (chronic obstructive pulmonary disease) or α1-proteinase inhibitor deficiency;

restrictive pulmonary diseases selected from among allergic alveolitis, restrictive pulmonary diseases triggered by work-related noxious substances, selected from asbestosis or silicosis, and restriction caused by lung tumours, selected from lymphangiosis carcinomatosa, bronchoalveolar carcinoma and lymphomas;

interstitial pulmonary diseases selected from among pneumonia caused by infection by viruses, bacteria, fungi, protozoa or helminths, pneumonitis caused by aspiration and left heart insufficiency, radiation-induced pneumonitis or fibrosis, collagenoses, selected from lupus erythematodes, systemic sclerodermy or sarcoidosis, and granulomatoses, selected from Boeck's disease, idiopathic interstitial pneumonia and idiopathic pulmonary fibrosis (IPF);

comprising administering to a patient in need thereof a therapeutically effective amount of the crystalline hydrochloride salt of N-(5-{2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide according to claim 1 in an inhalable powder formulation.

* * * * *

UNITED STATES PATENT AND TRADEMARK OFFICE
CERTIFICATE OF CORRECTION

| | | |
|---|---|---|
| PATENT NO. | : 8,394,791 B2 | Page 1 of 1 |
| APPLICATION NO. | : 12/918374 | |
| DATED | : March 12, 2013 | |
| INVENTOR(S) | : Werthmann et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 268 days.

Signed and Sealed this
Seventeenth Day of September, 2013

Teresa Stanek Rea
*Deputy Director of the United States Patent and Trademark Office*